(12) United States Patent
Davies et al.

(10) Patent No.: US 8,217,221 B2
(45) Date of Patent: Jul. 10, 2012

(54) CONTROLLED EVACUATION OSTOMY APPLIANCE

(75) Inventors: Geraint Davies, Cambridge (GB); John Cline, New Brunswick, NJ (US); Christopher C. Gregory, Newtown, PA (US); Alan Cucknell, Cambridge (GB); Julian Scarfe, Cambridge (GB); Pete Cauwood, Cambridge (GB)

(73) Assignee: ConvTec Technologies Inc., Las Vegas, NV (US)

( * ) Notice: Subject to any disclaimer, the term of this patent is extended or adjusted under 35 U.S.C. 154(b) by 0 days.

(21) Appl. No.: 11/563,462

(22) Filed: Nov. 27, 2006

(65) Prior Publication Data

US 2007/0123832 A1    May 31, 2007

Related U.S. Application Data

(60) Provisional application No. 60/741,091, filed on Nov. 30, 2005.

(51) Int. Cl.
*A61F 13/20* (2006.01)
*A61M 1/00* (2006.01)
*A61F 5/44* (2006.01)
*A61B 19/00* (2006.01)

(52) U.S. Cl. ........ 604/378; 604/322; 604/355; 604/356; 604/358

(58) Field of Classification Search ................ 600/562, 600/573, 575, 578, 581, 31, 309, 323, 322, 600/324, 325, 327, 328, 310, 473, 476, 478, 600/479, 623; 604/540, 541, 546, 523, 332, 604/337–339, 341–344, 348, 355

See application file for complete search history.

(56) References Cited

U.S. PATENT DOCUMENTS

| | | | | |
|---|---|---|---|---|
| 3,690,320 A * | 9/1972 | Riely | ............................. | 604/333 |
| 3,952,726 A * | 4/1976 | Hennig et al. | ................... | 600/30 |
| 4,210,131 A * | 7/1980 | Perlin | ............................. | 600/32 |
| 4,258,705 A * | 3/1981 | Sorensen et al. | ................. | 600/30 |
| 4,636,206 A * | 1/1987 | Ederati et al. | ................. | 604/340 |
| 4,721,508 A * | 1/1988 | Burton | ......................... | 604/338 |
| 4,723,952 A * | 2/1988 | Esposito | ...................... | 604/338 |
| 4,911,699 A * | 3/1990 | Fenton | ......................... | 604/333 |
| 4,941,869 A | 7/1990 | D'Amico | | |
| 4,950,223 A * | 8/1990 | Silvanov | ........................ | 600/32 |
| 4,964,858 A * | 10/1990 | Livny | ....................... | 604/385.21 |
| 4,983,171 A * | 1/1991 | Schirmer | ...................... | 604/332 |
| 5,045,052 A * | 9/1991 | Sans | ................................ | 600/32 |
| 5,178,614 A * | 1/1993 | McDowell et al. | ........... | 604/332 |
| 5,582,604 A * | 12/1996 | Ahr et al. | ................. | 604/385.12 |
| 5,643,234 A * | 7/1997 | Lesko | ........................... | 604/333 |
| 5,695,484 A * | 12/1997 | Cox | .............................. | 604/304 |
| 5,997,520 A * | 12/1999 | Ahr et al. | ................. | 604/385.12 |

(Continued)

FOREIGN PATENT DOCUMENTS

DE    2919467    10/1980

(Continued)

*Primary Examiner* — Leslie Deak
*Assistant Examiner* — Adam Marcetich
(74) *Attorney, Agent, or Firm* — Stuart E. Krieger

(57) ABSTRACT

A controlled evacuation ostomy appliance including a collection pouch, and an urging device for applying a sealing force through the pouch wall to seal the stoma. The pouch wall may seal directly against the stoma, or the pouch may have an internal sealing member that is pressed by the pouch wall against the stoma. The urging device provides an adjustable sealing force. The pouch may be disposable. The urging device may be reusable with a replacement pouch.

11 Claims, 7 Drawing Sheets

U.S. PATENT DOCUMENTS

| | | | |
|---|---|---|---|
| 6,332,879 B1 * | 12/2001 | Nielsen et al. | 604/344 |
| 6,485,476 B1 * | 11/2002 | von Dyck et al. | 604/332 |
| 6,506,184 B1 * | 1/2003 | Villefrance | 604/333 |
| 6,569,081 B1 * | 5/2003 | Nielsen et al. | 600/32 |
| 6,659,988 B1 * | 12/2003 | Steer et al. | 604/333 |
| 6,723,079 B2 * | 4/2004 | Cline | 604/337 |
| 2003/0181879 A1 * | 9/2003 | Mulhauser et al. | 604/332 |
| 2003/0187393 A1 * | 10/2003 | Cline | 604/131 |
| 2007/0021651 A1 * | 1/2007 | Gobel | 600/31 |
| 2007/0088300 A1 * | 4/2007 | Cline et al. | 604/342 |

FOREIGN PATENT DOCUMENTS

| | | |
|---|---|---|
| EP | 1346711 | 9/2003 |
| EP | 1348412 | 10/2003 |
| WO | WO9007311 | 7/1990 |

* cited by examiner

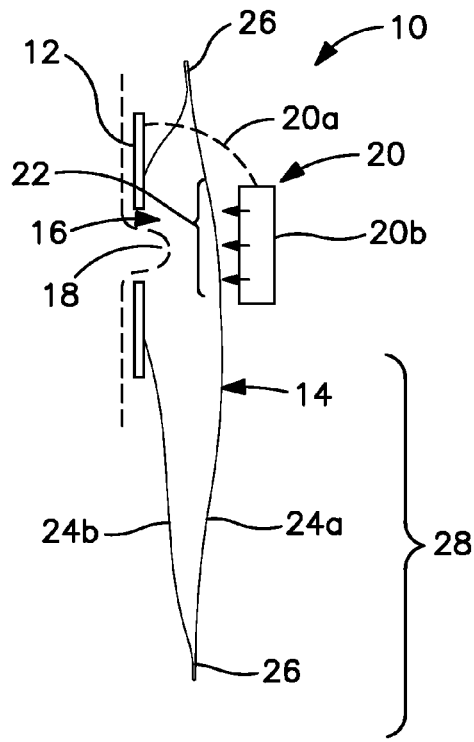
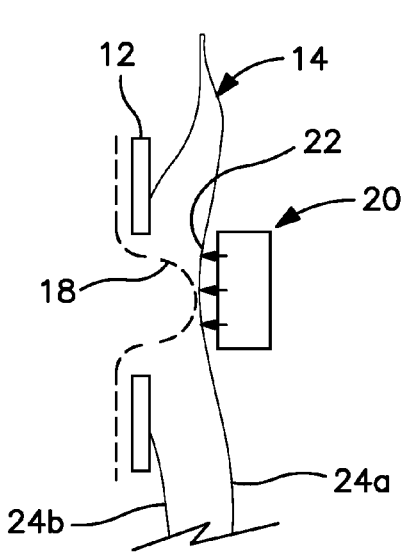 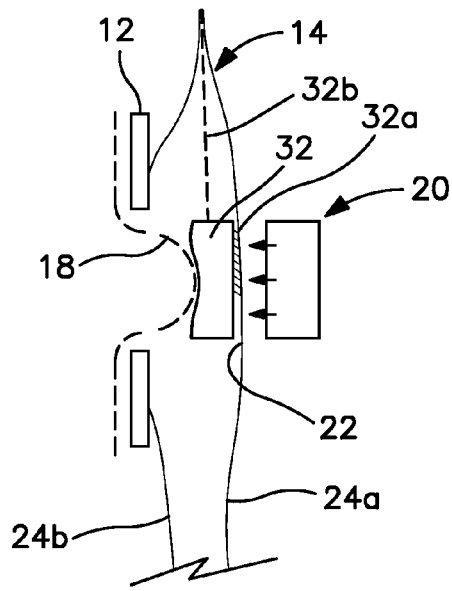
FIG. 1
FIG. 2
FIG. 3

CONTROLLED EVACUATION OSTOMY APPLIANCE

FIELD OF THE INVENTION

The present invention relates to the field of ostomy appliances, and in particular to such appliances which can be used to control stomal discharge (so called controlled evacuation appliances). One aspect of the invention relates to a seal for such an appliance for blocking the discharge of stool from the stoma.

BACKGROUND TO THE INVENTION

The creation of an ostomy (stoma) is the therapy for many sufferers of diseases or injury of the gastrointestinal or urinary tract. An ostomy is the rerouting of the tract through the abdominal wall to outside the patient's body. Once a stoma has been created, the patient must, frequently for the rest of his or her life, use a device worn on the body for capturing or containing the body waste. This has traditionally been done with a bag or pouch attached to the body with adhesive patches or constricting belts. However, the wearing of such a pouch can be an embarrassing a experience for many ostomates. A pouch may require significant changes in a person's public and personal activities.

A controlled evacuation appliance offers the potential for an ostomate to return to some form of normalcy. The appliance is used to block the stoma mouth, in order to retain the body waste temporarily inside the bowel. The appliance is deactivatable and/or removable manually when the ostomate desires to discharge the body waste from the stoma. A design feature which distinguishes a controlled evacuation appliance from a conventional ostomy pouch is the presence of a stoma seal, for blocking the stoma mouth. However, there are many practical and challenging difficulties associated with implementing a cost efficient, yet effective and comfortable stoma seal which has good customer acceptance. It is believed that this is one of the reasons why controlled evacuation appliances have hitherto not found widespread use.

SUMMARY OF THE INVENTION

One aspect of the invention is to provide an ostomy pouch with controlled evacuation capabilities, by using the inner face of the ostomy pouch wall as a seal surface, or a seal-bearing surface, for pressing directly or indirectly against a stoma to obstruct the discharge of at least a predetermined type of body waste. The inner face of the ostomy pouch wall is a face that, in use, faces towards the stoma. The inner face is the inner face of a front wall of the pouch, the exterior face of which may face away from the body in use.

In another aspect, an urging device provides an ostomy pouch with controlled evacuation capabilities. The urging device comprises a sealing force generating device. The urging device applies a sealing force to a stoma by means of the wall of the pouch, to effect a stoma seal. The urging device applies the sealing force to the stoma through the pouch wall. The urging device comprises a pressing device for pressing against the wall of the pouch to apply the sealing force through the pouch wall.

A controlled evacuation device provides a number of advantages:

(a) By using a pouch wall as a seal surface, or a seal-bearing surface, for a stoma seal, the ostomate is provided with enhanced controlled discharge capabilities while still using a pouch appliance which is similar to the conventional trusted pouches with which the ostomate is already familiar and comfortable. Familiarity of equipment can be important in gaining customer acceptance of emerging technologies in the field of ostomy, which is, by its nature, a highly personal and sometimes embarrassing experience for the ostomate.

(b) Since many of the components used in the appliance are similar to conventional pouch components, the design and manufacturing costs of a new appliance can be reduced.

(c) Furthermore, should any body waste leak (either by design or accidentally) past the stoma seal while in use, the leaked body waste can be contained within the pouch, thereby avoiding any risk of the body waste soiling the ostomate's skin or clothing.

As used herein, the term "stool" is used to mean any of solid, liquid, and semi-solid fecal matter. The term "body waste" is used to mean any body waste, for example, including stool and urine.

The inner face of the ostomy pouch itself acts as a seal surface in which case the inner face directly contacts the stoma. Alternatively, the inner face carries or bears against a sealing member, and the sealing member directly contacts the stoma, in use.

The seal created by contacting the stoma may be partly permeable, or otherwise configured so as to facilitate the escape of flatus, while obstructing the discharge of at least solid stool. This seal is configured (i) not to obstruct the escape of liquid stool (or other liquid body waste), or (ii) to allow the escape of liquid stool (or other liquid body waste) selectively when desired by the ostomate, or (iii) to obstruct the escape of liquid stool (or other liquid body waste).

The ostomy appliance comprises a device for pressing the inner face of the ostomy pouch wall towards and/or against the stoma. The device is controllable so that the pressing force is manually settable, adjustable and/or temporarily relievable. The appliance additionally or alternatively comprises a force-limiting device for limiting the pressing force that is applied when in use.

The device for pressing the pouch wall towards the stoma may be reusable. Even if the pressing device might be relatively expensive compared to the cost of an individual pouch, by making the pressing device re-usable, this relatively expensive component can be retained for multiple-uses enabling the pouch itself to remain a relatively cheap, disposable item.

Additional features and/or aspects of the invention are defined in the claims and/or apparent from the following description. Although certain features have been highlighted above and in the appended claims, claim protection may be sought for any inventive feature and/or idea described herein and/or illustrated in the drawings, whether or not emphasis has been placed thereon.

BRIEF DESCRIPTION OF THE DRAWINGS

FIG. 1 is a schematic view of selected features in the controlled evacuation ostomy appliances of the preferred embodiments.

FIG. 2 is a schematic view of a first type of embodiment.

FIG. 3 is a schematic view of an alternative type of embodiment with a discrete sealing member.

DETAILED DESCRIPTION OF PREFERRED EMBODIMENTS

Figure 4:
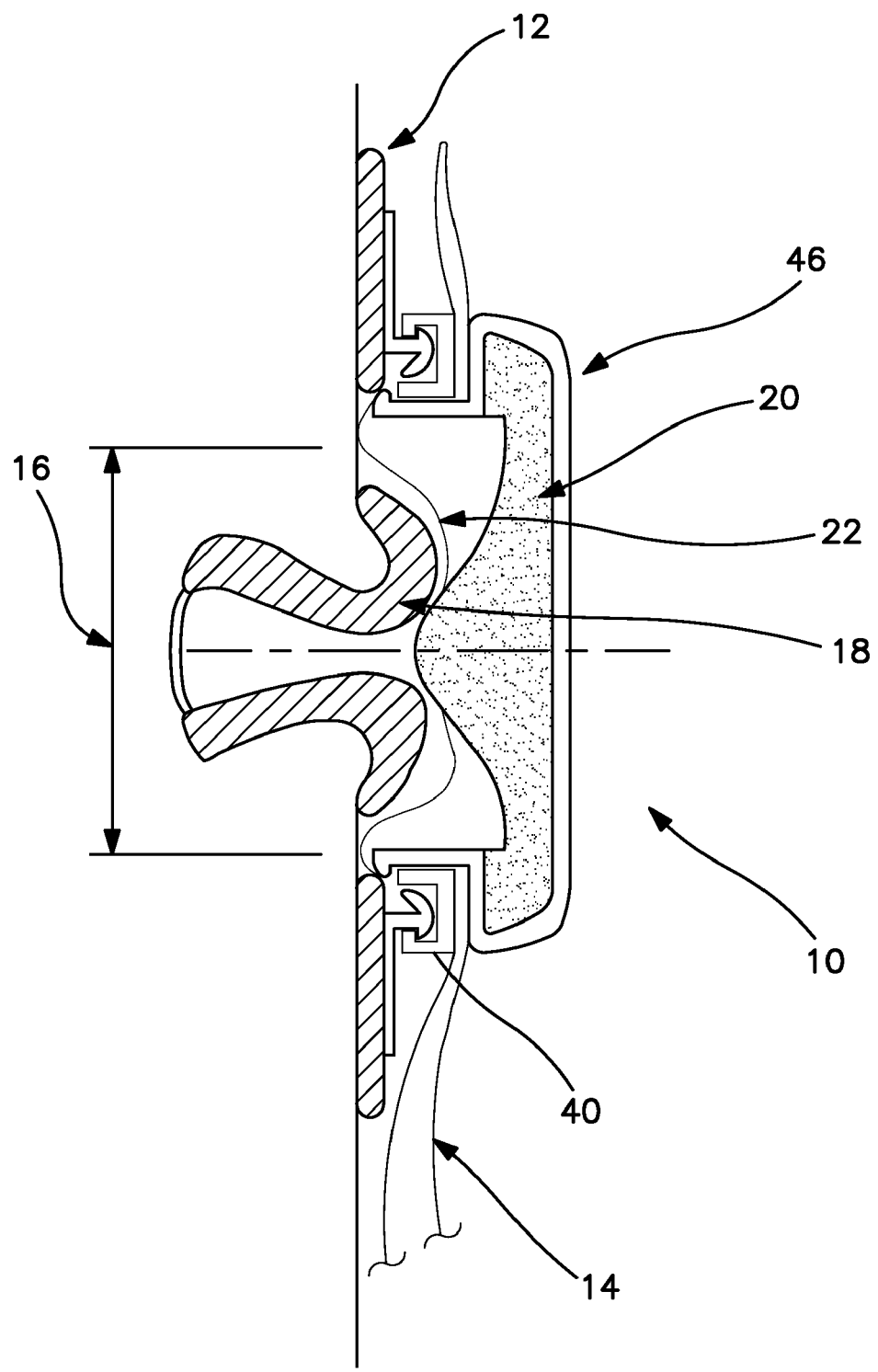
FIG. 4 is a schematic view of an example of a controlled evacuation appliance.

Referring to the FIGS. 1-7, the appliance 10 generally comprises: a body attachment 12 for securing the appliance 10 in use against a wearer's body; a collection pouch 14 having a stoma aperture 16 for communicating with the wearer's stoma 18; and an urging device 20 for urging a portion 22 of the pouch 14 opposite the stoma aperture 16 towards the stoma aperture 16 and the stoma 18 in use to directly or indirectly form a seal against the stoma 18. The urging device 20 is adjustable, to enable adjustment of the urging force, so as to achieve an effective seal without pressing too hard against the stoma 18. The urging device 20 is removable, controllable or manipulable to enable the urging force to be at least temporarily removed or relieved, to thereby enable a controlled discharge of body waste from the stoma 18 into the pouch 14.

By using a pouch portion 22 as a seal surface, or a seal-bearing surface, for a stoma seal, the ostomate is provided with enhanced controlled discharge capabilities while still using a pouch appliance which is similar to the conventional trusted pouches with which the ostomate is already familiar and comfortable. Also, some of the components of the appliance 10 may be similar to those used with conventional pouches, which can avoid the need for expensive redesign and new manufacture. Moreover, any leakage of body waste from the stoma 18 (whether by design as discussed later below, or by accident) is contained within the pouch 14, and thus avoids soiling of the ostomate's skin and clothing.

Before any discharge of body waste into the pouch 14, the pouch 14 is substantially flat. This enables the appliance 10 to be worn in a very discrete manner under the ostomate's clothing, even if the pouch 14 is relatively large compared to the stoma 18. Moreover, since the user controls the discharge of body waste into the pouch 14, the pouch 14 keeps its flat, empty state for a considerable time, which is a vast improvement compared to a conventional pouch without controlled evacuation capabilities. Furthermore, the pouch 14 of the present appliance 10 may, optionally, be initially provided in a reduced size, stowed condition (not shown). For example, a lower portion 28 of the pouch 14 may be folded or rolled-up, so that the pouch 14 does not occupy its full height. This enables the appliance 10 to be extremely compact when first used, similar to a stoma plug, and considerably smaller than a conventional pouch. The ostomate releases the pouch 14 to deploy the pouch 14 to its full height (e.g., full capacity) prior to a discharge of body waste into the pouch 14.

The urging device 20 may, optionally, be a re-usable unit. The urging device 20 is separable from the pouch 14 to enable the pouch 14 to be disposed of, and to enable the urging device 20 to be re-used with a replacement pouch 14. This enables the additional production costs of the urging device 20 to be spread with respect to the costs of several pouches. The urging device 20 may be disposed generally outside the pouch 14 (or at least outside the body-waste containing portion of the pouch 14), to avoid having to clean the urging device 20 between uses. For example, the urging device 20 may be releasably securable to the body attachment 12.

The urging device 20 comprises an anchoring portion 20a for supporting the opposite reaction to the urging force, and a pressing portion 20b for bearing against the pouch wall portion 22.

The body attachment 12 is a single unit that is permanently attached to the appliance 10 (a so-called "one piece" appliance), or the body attachment 12 may include one or more separable parts, e.g., a separable adhesive bearing pad (not shown), that may be attached to the body to provide a reusable fixing point for a mechanical or adhesive attachment of the appliance 10 to the pad (a so-called "two piece" appliance).

The pouch 14 comprises one or more walls 24a, 24b, each comprising one or more flexible sheets. The sheets are made of plastics or any other suitable thin, flexible material. Each sheet comprises a laminate including a barrier layer for obstructing diffusion of gas through the material. When a wall 24a, 24b comprises multiple sheets, the sheets may, for example, be discrete and separate, and be mutually attached at or around a periphery 26 of the pouch 14. In a particular pouch construction, the pouch 14 is in "envelope" form, e.g., consisting of a front wall 24a and a rear wall 24b joined at their edges. The front and rear walls 24a, 24b may be formed from separate sheets of material sealed together around their periphery 26, or from a single sheet of material folded and sealed around the open periphery 26. Other styles and constructions of pouch are also envisaged. The pouch 14 may be closed ended such that it is not intended to be drainable. Alternatively, the pouch 14 may include a drain outlet, similar to urostomy and/or ileostomy pouches. Depending on the design criteria, the pouch 14 may resemble a conventional ostomy pouch in terms of size and/or appearance, or the pouch 14 may differ substantially from a conventional ostomy pouch.

The portion 22 of the pouch 14 urged by the urging device 20 is a portion of the front wall 24a. In the embodiment illustrated in FIG. 2, the wall portion 22 directly contacts the stoma 18 to form a direct seal thereagainst. In this embodiment, the wall material itself provides the seal properties. In the embodiment illustrated in FIG. 3, a sealing member 32 is mounted inside the pouch 14 such that the wall portion 22 forms an indirect seal against the stoma 18 by means of the sealing member 32. The sealing member 32 is either carried by or attached to the wall portion 22 (as illustrated by schematic attachment 32a), or it may be suspended by another support (as illustrated by schematic support curtain 32b) within the pouch 14 such that the wall portion 22 can bear against the sealing member 32 to urge it against the stoma 18.

The nature of the seal formed by the wall material or by the sealing member 32, relative to the stoma 18, is configured according to properties desired for the appliance 10. In one form, it is preferred that the seal be capable, as a minimum, of retaining solid stool within the stoma 18 at least while the urging device 20 urges the wall portion 22 towards the stoma 18.

The seal may be liquid-tight, or it may partly or generally allow the passage of liquid therepast (i.e., through or around the seal). A liquid tight seal requires that (i) the material used for the seal face be liquid impermeable, and (ii) the seal be able to form a substantially liquid-tight fit at the interface with the stoma 18. On the other hand, a seal that at least partly allows the passage of liquid comprises liquid-permeable material to allow liquid to pass therethrough and/or therein (e.g., for lateral permeation of liquid within the material without passing from one side of the material to the other). Additionally, a seal that at least partly allows the passage of liquid may have a surface that does not, in use, form a liquid-tight fit with the stoma 18, such that liquid may "leak" laterally at the interface between the seal and the stoma 18. It is preferred that any liquid that escapes from the stoma 18 (either accidentally or intentionally by design of the seal) flow into the interior of the pouch 14. Thus, in the case of the wall portion 22 forming a direct seal (as in FIG. 2), it is preferred that the wall 24*a*, 24*b* itself be liquid impermeable in the sense of blocking liquid flow from one side of the wall 24*a*, 24*b* through the wall material to the other side.

The seal may be gas-tight, or it may partly or generally allow the passage of gas therepast in order to facilitate venting of flatus from the stoma 18. A gas-tight seal requires that (i) the material used for the seal face be gas impermeable, and (ii) the seal be able to form a substantially gas-tight fit at the interface with the stoma 18. On the other hand, a seal that partly allows the passage of gas may comprise gas-permeable material to allow gas to pass therethrough and/or therein (e.g., for lateral permeation of gas without passing from one side of the material to the other). Additionally, a seal that partly allows the passage of gas may have a surface that does not, in use, form a gas-tight fit with the stoma 18, such that gas may "leak" laterally at the interface between the seal and the stoma 18. It is preferred that any gas that escapes at the stoma 18 passes into the interior of the pouch 14, for example, if the pouch 14 has a separate gas vent (not shown), such as a vent with a deodorizing filter. Additionally, the wall portion 22 may be gas permeable to provide a direct outlet vent for flatus from the pouch.

In some designs of the appliance 10, at least one item of the sealing member 32 (if provided), and the pressing portion 20*b* of the urging device 20, may be conformable, to enable the seal to adapt to the shape of the stoma 18, and to avoid localized pressure points that might cause discomfort or result in damage to the stoma tissue. The item may be custom shaped to fit the stoma 18, in which case the item might have only a small degree of conformity. Alternatively, the item may have a non-custom shape, and be substantially conformable to fit an individual's stoma. The item may be resiliently conformable. In a case where the urging device 20 does not generate a uniformly distributed force, the sealing member 32 acts as an intermediate member that can distribute this force as a more even sealing force against, or around, the stoma 18.

Various possible forms of the sealing member 32, and/or the pressing portion 20*b* of the urging device 20, are now described by way of example:

In one form, the urging device 20 comprises a sheet of elastomeric material which is pulled under tension towards the stoma 18.

In a somewhat similar manner, the sealing member 32 comprises a special elastomeric layer (or liner) that is very flexible in order to form a better seal than a conventional pouch wall material. The elastomeric layer may itself not be suitable as a principal feces-containing layer of the entire pouch 14. The elastomeric layer may be disposed only in the region facing the stoma 18, or the elastomeric layer may extend the entire height of the pouch 14, and be disposed as an inner layer or liner of the front wall 24*a*.

In another form, the sealing member 32, and/or the pressing portion 20*b* of the urging device 20, comprises an object which is formed to have substantially a complementary shape to the stoma 18. The object 20*b* is somewhat flexible or conformable in order not to create local pressure points on the stoma 18 and, for example, may be a custom shaped block of low-flexibility foamed polymer, or a resilient solid material such as silicon rubber.

The object may be made to match the shape of the stoma 18 by using a foam-into-place material (such as used in ski-boot customizing) or a settable liquid contained within a bag. The liquid is a mix-to-activate 2-part epoxy, or a wax which is slightly heated to melt or mobilize it and then sets as it cools against the stoma 18. To shape the object 22*b*, it is pressed gently against the stoma 18 (e.g., through the pouch wall or another protective membrane) while setting.

Alternatively, the sealing member 32, and/or the pressing portion 20*b* of the urging device 20, comprises a highly conformable object, such as visco-elastic foam, similar to the type used in earplugs, a moldable material such a foamed PTFE, a loose-bag containing small smooth beads or balls, or an inflatable conformable chamber. The inflation fluid is any suitable gas or liquid.

In the case of an inflatable chamber, if the material defining the chamber is highly elastic, it allows the pressure to remain somewhat independent of constrained containment of the chamber as it is pressed against the stoma 18. Alternatively, if the material of the inflatable chamber is not highly elastic, the pressure it achieves may be set within a desired range in order to achieve a desired seal against the stoma 18, in particular, sufficiently high to avoid leaks, yet not so high as to risk damaging the stoma tissue. Example means for setting the inflation pressure (especially, but not exclusively, suitable for the externally mounted pressing portion 20*b*) include:

(a) a pressure relief valve to release any excess pressure;
(b) a device for changing the chamber volume, for example, by folding or rolling up a portion of the chamber, and thus change the internal pressure accordingly;
(c) a valve for accepting inflation fluid from an external pump, or from a tube for oral inflation, or from a syringe pump; and/or
(d) a multiplicity of pre-inflated bags held together in a confining manner, such as being contained within a net. One or more of the bags may be rupturable or deflatable to reduce the overall pressure applied by the assembly of bags to a desired value.

If pressurized chambers are kept and used for prolonged periods of time, rather than disposed of daily, then the chambers may be configured to prevent, or at least reduce, the effects of deflation by diffusion of the inflation fluid through the chamber wall. Suitable techniques include metalized or glossy coatings that act as diffusion barrier layers, or the use of large-molecule gases such as flurocarbons as the inflation gas.

The chamber or bags may be non-inflated during transport, and then pressurized to a certain value at the point of use. For example, the chamber or bags may contain mix-to-activate effervescent materials (such as predetermined quantities of weak acid, and a carbonate) which the user activates by rubbing the chamber in their fingers.

Where foam is used for forming the sealing member 32, the foam may be closed-cell foam to be impermeable, or open-cell foam to be at least partly permeable, or it may be of open-cell foam that is skinned with an impermeable skin.

Various forms of anchoring portion 20*a* of the urging device 20 are envisaged. The purpose of the anchoring portion 20*a* is to support the opposite reaction force to the urging force applied by the pressing portion 20*b*. The anchoring portion 20*a* attaches the urging device 20 to the wearer's body, the body attachment 12, or other appliance 10 components, in order to anchor the urging device 20 in position. For example, the anchoring portion 20*a* may comprise any of: a belt worn by the ostomate; an adhesive pad for attaching to the wearer's skin; or a coupling member for coupling to the body attachment 12.

A feature of the urging device 20 is that the urging force is adjustable, either during setting up of the appliance 10, or during wear by the ostomate. For example, the urging force may be increased if the user experiences concern for a leak and/or the urging force may be decreased if the user feels discomfort. Such adjustment is provided, for example, by adjusting the inflation pressure of an inflatable chamber, as explained above. The adjustment may also be provided by an anchoring portion 20a including relatively adjustable positioning. The positioning of the anchoring portion 20a may be adjusted, for example, by threaded movement of one of more screw threads.

An additional feature of the urging device 20 is that the urging force be temporarily relievable, for example, by lifting the urging device 20 away from contact with the pouch wall portion 22. Such adjustment, or relief, is implemented within the anchoring portion 20a and/or the pressing portion 20b.

A further additional or alternative feature of the urging device 20 is a force limiting device for limiting the maximum sealing force exerted by the urging device 20. For example, such a force limiting device is implemented by a pressure relief valve of an inflatable chamber, or by a torque-limiting arrangement of a screw threaded force adjustment device, or by a spring member configured to deflect when the urging force reaches a predetermined threshold. For example, the spring member is a constant force type spring, such as an unwinding flat coil (or Negator) spring or an Euler beam spring.

The following examples illustrate, in more detail, specific appliance constructions, based on the aforementioned techniques.

Figure 4A:
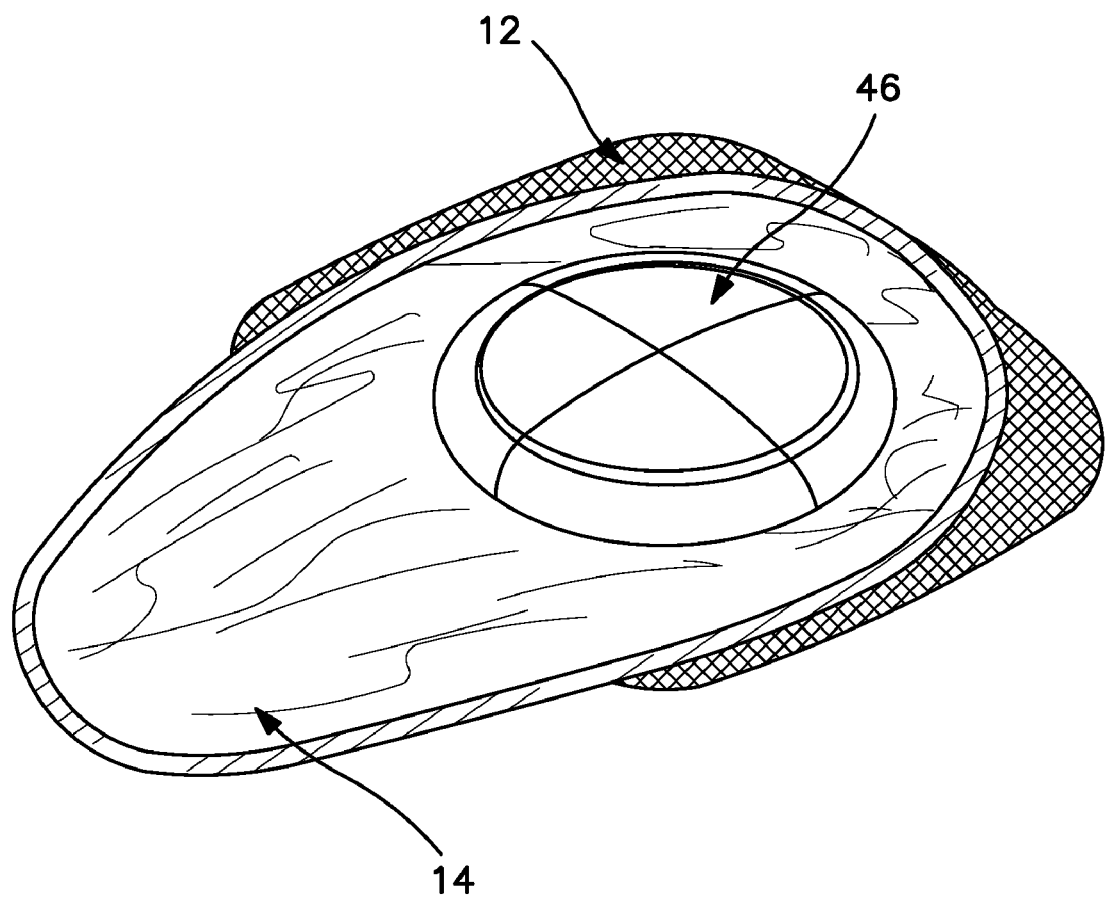
FIG. 4a is a perspective view of the top of a controlled evacuation appliance.

FIGS. 4 and 4a illustrate an example of a controlled evacuation appliance 10. The appliance 10 comprises a body attachment 12 in the form of an adhesive wafer or plate, and has a coupling portion 40 for releasably mounting the pouch 14 thereon. The coupling portion 40 typically comprises a ring shaped fitting for mechanical engagement with a complementary coupling portion of the pouch, but many other coupling types are envisaged. In this example, the pouch 14 does not have an internal sealing member 32. The urging device 20 generally comprises a cap 46 that is securable over the front of the pouch 14, in register with stomal aperture 16. The urging device 20 includes a shaped pressing portion, the shape including a central bulge configured for pressing the wall portion 22 of the pouch 14 against a stoma 18, for sealing the stoma 18 to obstruct the discharge of body waste therefrom. The pressing portion of the urging device 20 may, for example, be made of a resilient foam material. The urging device 20 is supported on the body attachment 12 either by means of the same coupling 40 as the pouch, or by a separate coupling (not shown). Such a separate coupling may, for example, comprise a screw threaded, or bayonet-type fastener.

In use, when the ostomate desires to evacuate body waste from his stoma, the ostomate releases the urging device 20 from the body attachment 12, thus removing the sealing force applied to the pouch wall portion 22. Body waste is therefore free to discharge from the stoma 18 into the pouch 14.

Figure 5:
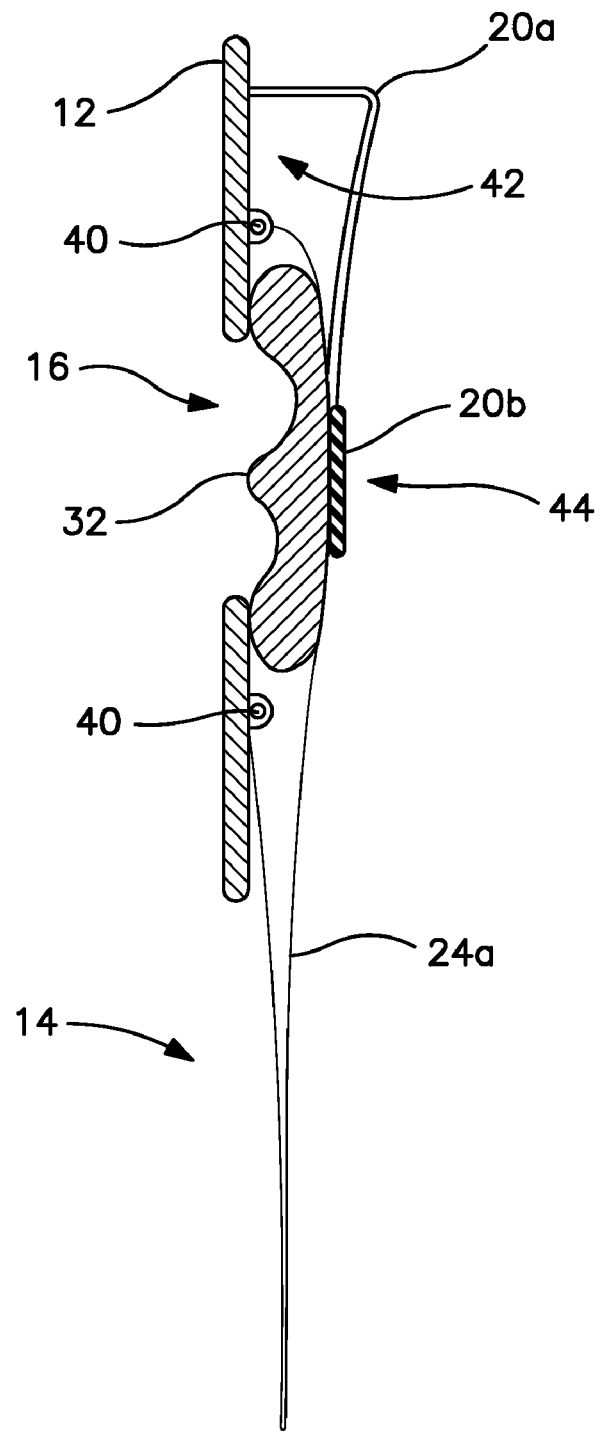
FIG. 5 is a schematic view of another example of a controlled evacuation appliance.

Referring to FIG. 5, in another example of the appliance 10, the pouch 14 comprises a sealing member 32 positioned in the pouch 14 adjacent to the stomal aperture 16. The sealing member 32 has the same type of shape as described above. The urging device 20 includes one or more cantilever arms 20a, terminating in a pressing portion 20b. The cantilever arm 20a is permanently or removably mounted on the body attachment 12. The reaction of the urging force 44 is applied as a force at the position indicated by arrow 42, tending to lift the adhesive from the wearer's skin. If only one cantilever arm 20a is provided, then care is needed in the design of the body attachment 12 to ensure that body attachment 12 is fastened sufficiently firmly to the skin so that it will not peel away under the reaction force that is applied substantially entirely at one position corresponding to the single cantilever arm 20a. Using a plurality of cantilever arms 20a enables the reaction force to be distributed at multiple points.

Figure 6:
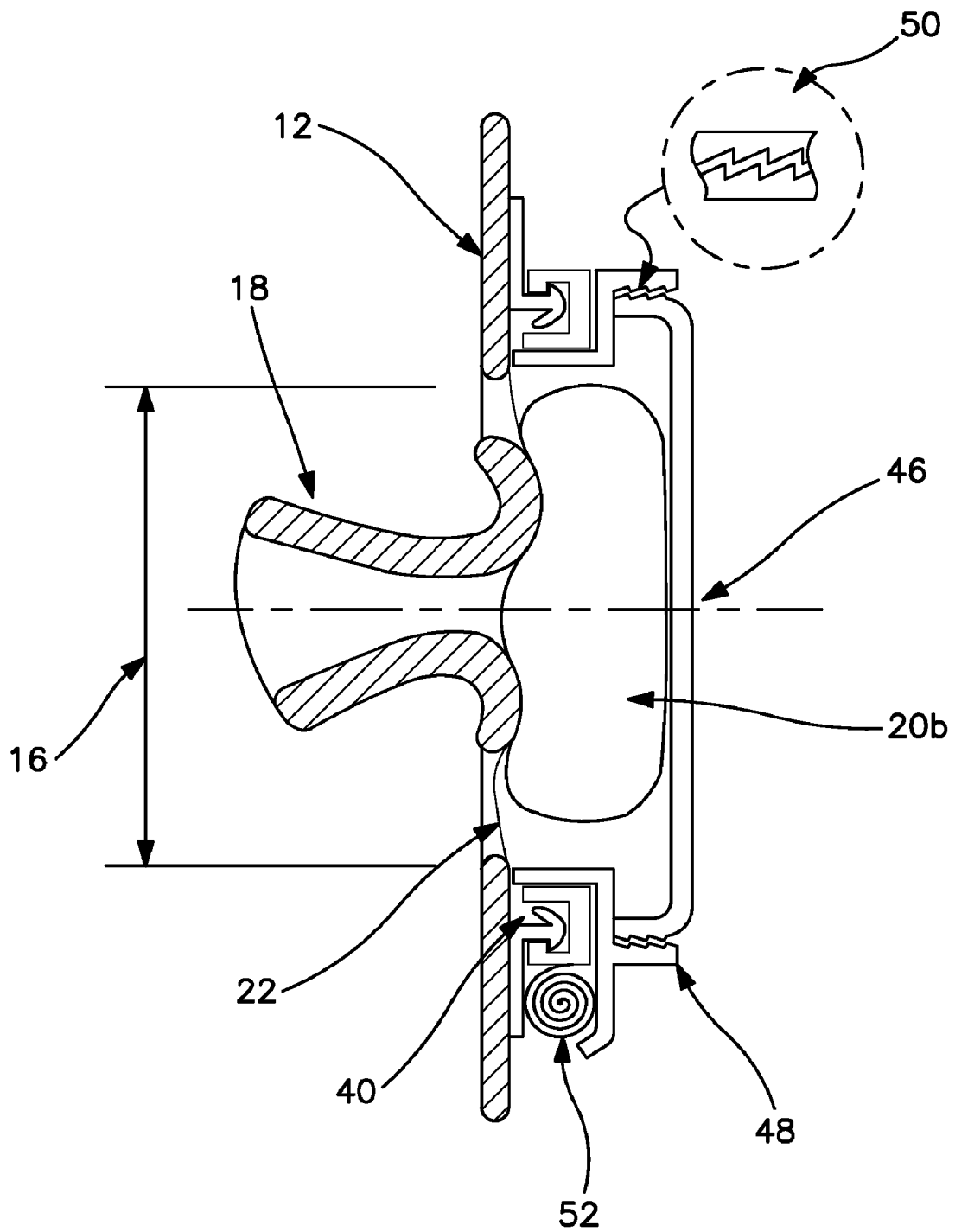
FIG. 6 is a schematic view of an additional example of a controlled evacuation appliance.
Figure 7:
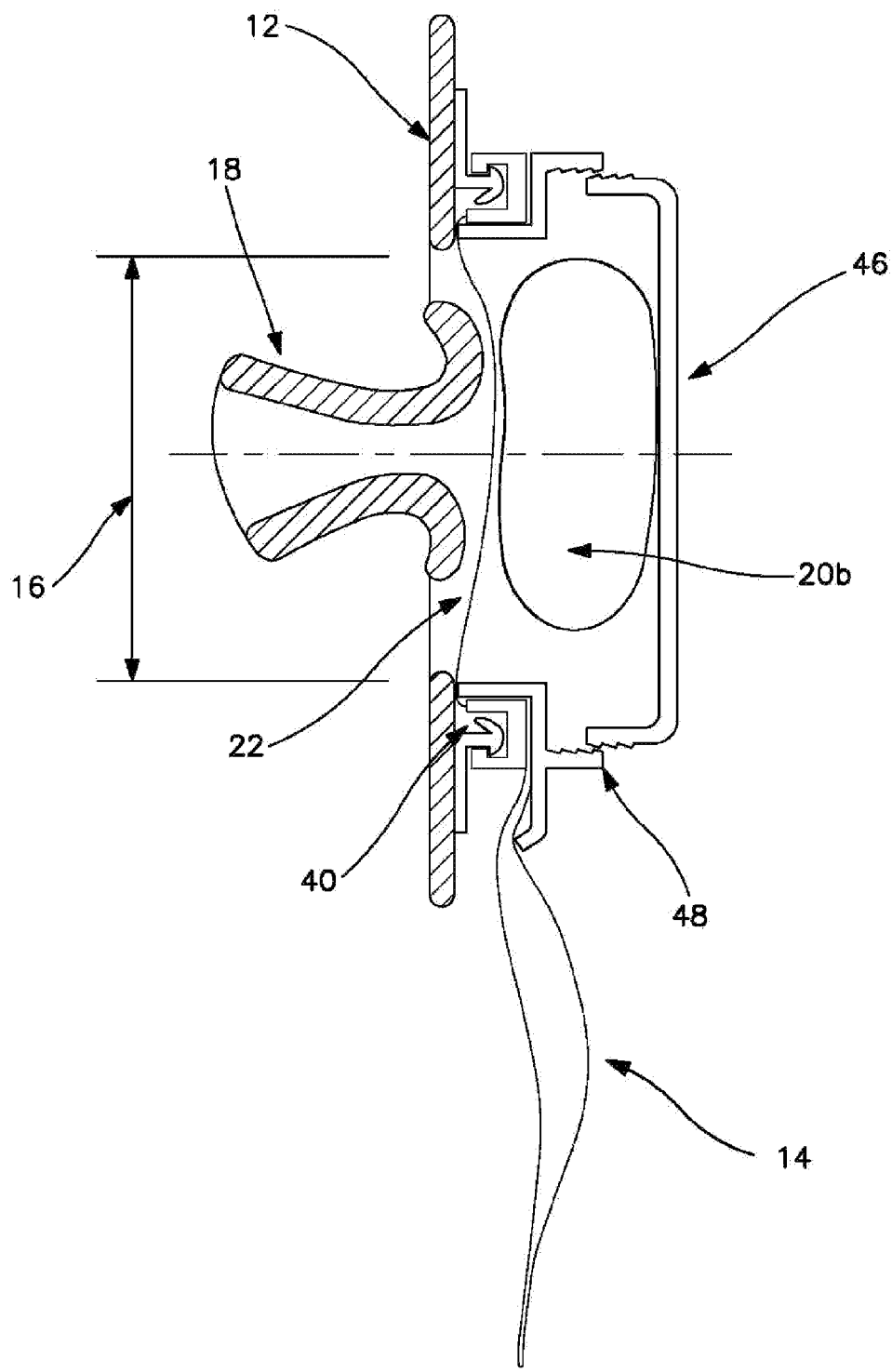
FIG. 7 is a schematic view of an additional example of a controlled evacuation appliance.
Figure 7A:
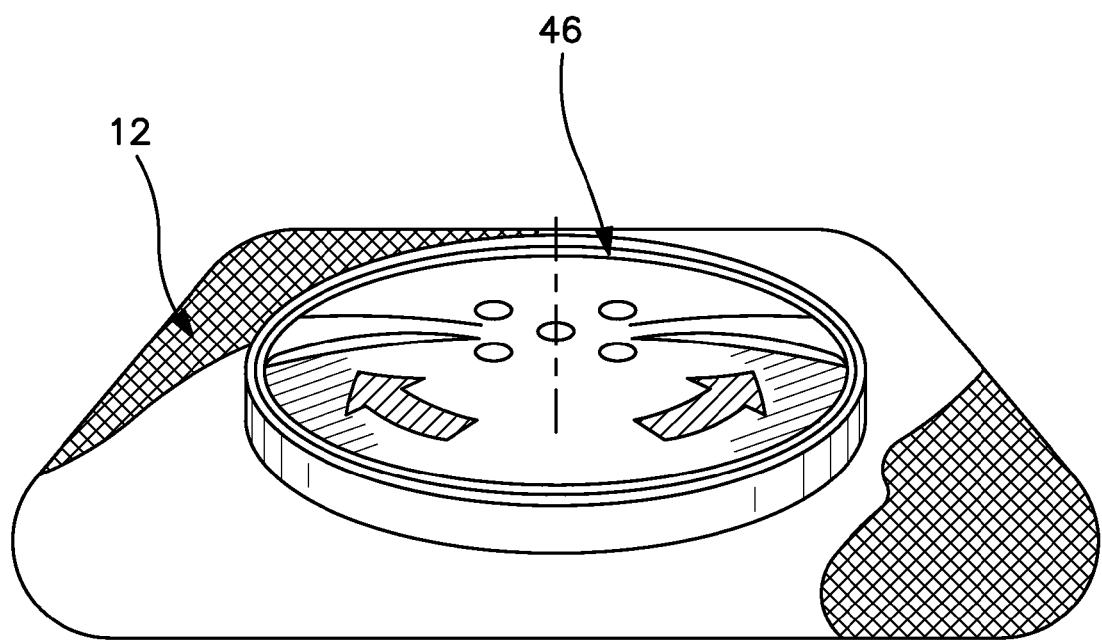
FIG. 7a is a perspective view of the top of a controlled evacuation appliance.

Referring to FIGS. 6, 7 and 7a, in an additional example of a controlled evacuation appliance 10, the pouch 14 does not include any sealing member. The pressing portion 20b of the urging device 20 comprises an inflatable chamber. The urging device 20 further comprises a screw-threaded cap 46 mounted on a threaded ring 48. The inflatable chamber may be pre-inflated, and the sealing force regulated by rotating the cap 46 relative to the ring 48, to tighten or un-tighten the cap 46. When the cap 46 is tightened (see FIG. 6), it moves towards the stomal aperture 16, and, hence, increases the pressure in the inflatable chamber and thus increases the sealing force applied to the stoma 18. When the cap 46 is untightened (see FIG. 7a), it moves away from the stomal aperture 16, and, hence, decreases the pressure in the inflatable chamber and thus decreases the sealing force applied to the stoma. By rotating the cap 46 to completely untighten it, the sealing pressure is removed, and body waste is allowed to discharge into the pouch 14.

Referring to the inset partial figure of FIG. 6, one or both of the screw threads 50 of the cap 46 and the ring 48 is formed as a torque-limiting thread. The thread has a ramp profile, such that, when the torque exceeds a predetermined threshold, the threads slip in the axial direction to relive the torque.

As illustrated at 52 in FIG. 6, the pouch 14 initially is rolled into a compact size, and at least partly stored within the cap 46. Upon untightening the cap 46, the pouch 14 drops down, or distends, through an opening between the ring 48 and the cap 46, as shown in FIG. 7. The same principle may also be implemented in the examples illustrated in FIGS. 4 and 5.

We claim:

1. A controlled evacuation ostomy appliance comprising:
   a. an ostomy pouch having two thin flexible walls, a front wall and a rear wall, said rear wall having a stomal aperture for fitting around a wearer's stoma, said front wall being opposite said stomal aperture, said front wall having an outside surface and inside surface;
   b. a non-rupturable sealing member fully located and secured within said pouch and secured within said pouch to said inside surface, said sealing member being resiliently conformable to the stoma and effecting a stomal seal by resiliently conforming in sealing contact with the stoma when a suitable sealing force is applied thereto, wherein the sealing member comprises a foam member or a multiplicity of loosely captive particles; and
   c. an incrementally adjustable urging device located outside of and in direct contact with said outside surface of said front wall of said pouch, said incrementally adjustable urging device being configured to contact against said outside of said front wall opposite the stomal aperture and transmit and apply an incrementally adjustable and suitable sealing force from said outside surface directly through said front wall to said sealing member by said contact against said front wall, said sealing force being temporarily relievable by said incrementally urging device.

2. The ostomy appliance according to claim 1, wherein said sealing member is carried by said pouch wall.

3. The ostomy appliance according to claim 1, wherein said adjustable urging device comprises a pressing portion for pressing against said front pouch wall to exert said sealing force there against.

4. The ostomy appliance according to claim 3, wherein said pressing portion is at least partly conformable and comprises at least one of the following: a foam member; an inflatable or inflated chamber; a multiplicity of loosely captive particles.

5. The ostomy appliance according to claim 1, wherein said adjustable urging device comprises an anchoring portion for anchoring said adjustable urging device, and for supporting the reaction to said sealing force applied by said urging device.

6. The ostomy appliance according to claim 1, wherein said adjustable urging device is configured to enable the user to relieve said sealing force by manipulation of the adjustable urging device, to relieve said stomal seal.

7. The ostomy appliance according to claim 6, wherein said adjustable urging device is configured to enable the user to relieve said sealing force temporarily to permit a stomal discharge, and to reapply said sealing force thereafter.

8. The ostomy appliance according to claim 1, wherein said adjustable urging device comprises a force limiting device for preventing said sealing force from exceeding a predetermined threshold.

9. The ostomy appliance according to claim 1, wherein said stomal seal is effective to block the discharge of at least solid body waste.

10. The ostomy appliance according to claim 9, wherein said stomal seal is effective to allow the discharge of flatus gas from the stoma, while blocking the discharge of at least solid body waste.

11. The ostomy appliance according to claim 1, wherein said adjustable urging device is separable from the pouch, and is reusable with a replacement pouch.

\* \* \* \* \*